(12) United States Patent
Heller (10) Patent No.: US 10,101,051 B2
(45) Date of Patent: Oct. 16, 2018

(54) SYSTEM AND PROCESS FOR NOTIFICATION OF CONTAGION RISK CONDITIONS AND MITIGATION THEREOF

(71) Applicant: Wello, Inc., Dallas, TX (US)

(72) Inventor: Alan C. Heller, Dallas, TX (US)

(*) Notice: Subject to any disclaimer, the term of this patent is extended or adjusted under 35 U.S.C. 154(b) by 277 days.

(21) Appl. No.: 14/890,297

(22) PCT Filed: May 10, 2014

(86) PCT No.: PCT/US2014/037603
§ 371 (c)(1),
(2) Date: Nov. 10, 2015

(87) PCT Pub. No.: WO2014/183100
PCT Pub. Date: Nov. 13, 2014

(65) Prior Publication Data
US 2016/0109149 A1    Apr. 21, 2016

Related U.S. Application Data

(60) Provisional application No. 61/928,997, filed on Jan. 17, 2014, provisional application No. 61/822,136, filed on May 10, 2013.

(51) Int. Cl.
*G05B 15/00* (2006.01)
*F24F 11/00* (2018.01)
(Continued)

(52) U.S. Cl.
CPC .......... *F24F 11/0015* (2013.01); *F24F 11/30* (2018.01); *G05B 15/02* (2013.01);
(Continued)

(58) Field of Classification Search
CPC ... F24F 11/0015; G05B 15/02; G06F 19/3493
(Continued)

(56) References Cited

U.S. PATENT DOCUMENTS 4,880,581 A    11/1989 Dastoli et al.
6,154,143 A    11/2000 Robinson
(Continued)

FOREIGN PATENT DOCUMENTS

WO    WO 02/063539    8/2002

*Primary Examiner* — Vu A Vu
(74) *Attorney, Agent, or Firm* — John Lindsay (57) ABSTRACT

The present invention is directed to system and process for notification of contagion risk and mitigation of the risk thereof. The system comprises a meteorological history repository having meteorological data and a processor configured with an instruction set. The instruction set includes retrieving meteorological data for a selected region for a selected time window, calculating contagion risk based on the meteorological data and from at least one of a transmission risk or a susceptibility risk, calculating the transmission risk as a function of dew point change and calculating susceptibility risk as a function of relative humidity. The system generates a contagion risk indicator based thereon. Embodiments of the system for mitigating the risk of spread of contagions and include a controller configured to select a lower humidity bound as a function of contagion infectivity and an upper humidity bound as a function of contagion viability or mold/fungus growth rate. The controller receives humidity data for the sealed area and issues control signals to a humidification unit in response to the received humidity data and according to the selected lower humidity bound and the upper humidity bound.

4 Claims, 12 Drawing Sheets

(51) Int. Cl.
    *G05B 15/02*    (2006.01)
    *F24F 11/30*    (2018.01)
    *G16H 50/80*    (2018.01)
    *G06F 19/00*    (2018.01)
    *F24F 110/20*   (2018.01)

(52) U.S. Cl.
    CPC ............. *G06F 19/00* (2013.01); *G16H 50/80* (2018.01); *F24F 2110/20* (2018.01)

(58) Field of Classification Search
    USPC ........................................................ 700/276
    See application file for complete search history.

(56)               References Cited

U.S. PATENT DOCUMENTS 6,181,260  B1*   1/2001  Simon .................... G01W 1/10
                                                         340/945
    8,112,181  B2*   2/2012  Remsburg ............ F24F 11/0015
                                                         700/276
    2010/0317377  A1   12/2010  Zou
    2012/0020830  A1    1/2012  Boast et al.
    2013/0130227  A1*   5/2013  Peltz ................... G06F 19/3493
                                                         435/3

\* cited by examiner

Figure 9A:
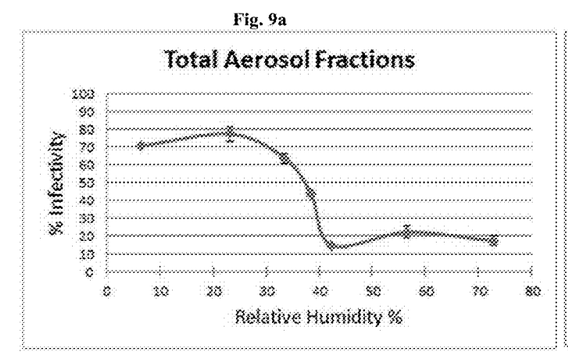

Fig. 9a Total Aerosol Fractions

Fig. 9b 1-4 µM Fraction

Figure 9B:
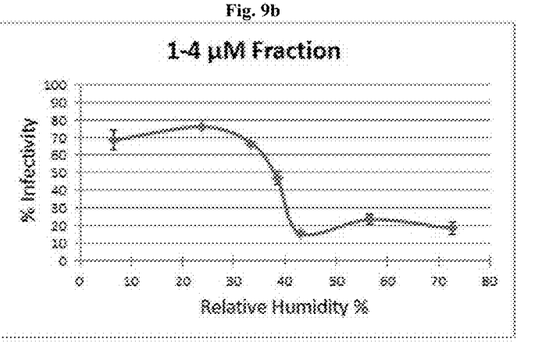
Figure 9C:
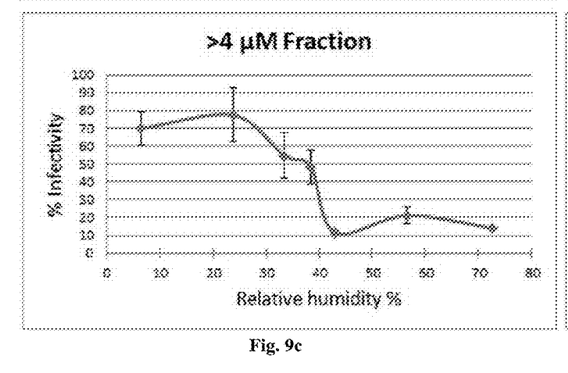

Fig. 9c >4 µM Fraction

Figure 9D:
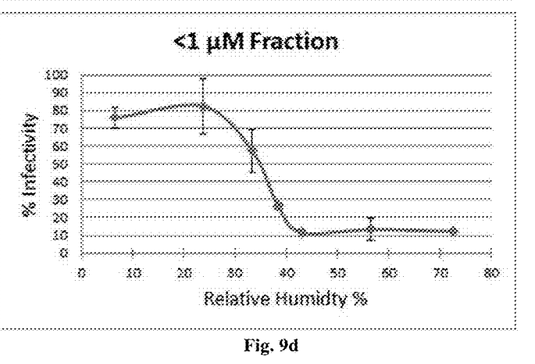

Fig. 9d <1 µM Fraction

SYSTEM AND PROCESS FOR NOTIFICATION OF CONTAGION RISK CONDITIONS AND MITIGATION THEREOF

PRIORITY

The present invention claims priority to provisional application 61/822,136, which has a filing date of May 10, 2013. The present invention claims priority to provisional application 61/928,997, which has a filing date of Jan. 17, 2014.

BACKGROUND

Field of the Invention

The present invention relates to a system and process for notification of potential health conditions, more specifically to a system and process for notification of contagion risk conditions and mitigation thereof.

Description of the Related Art

A humidifier is generally an appliance that increases humidity in a single room, house, or building. Common humidifiers include point-of-use humidifiers, which are commonly used to humidify a single room, and whole-house or furnace humidifiers, which connect to a home's HVAC system to provide humidity to the entire house. Humidifiers are often used to relieve dry and scratchy lips and skin, help asthma suffers by providing moisture for the respiratory system, decrease furnace use due to humidified air's warmer feeling, and preventing uncomfortable static shock that causes electronic equipment to fail by reducing the static electricity in the room. However, it is known that overuse of a humidifier or the high humidification of indoor air with forecast increase in dewpoint can raise the relative humidity to high levels, promoting the growth of dust mites, the viability of contagion, mold, fungus, and maladies such as "humidifier lung."

A dehumidifier is generally a household appliance which reduces the level of humidity in the air, usually for health reasons. Higher humidity air can cause mold and mildew to grow inside the excessively humid environment, both of which pose health risks. A dehumidifier can also connect to a home's HVAC system to provide dehumidified air to the entire building.

While the humidifier and dehumidifier can generally impact health conditions, the art has yet to apply them to function in a zone that in order to warn and minimizes spread of a wide spectrum of contagions. In disease transmission, two key person-to-person possible transmission routes include airborne transmission and indirect transmission via fomites. In airborne transmission, the pathogen is may be spread through exhalation, coughing, sneezing, or similar actions, where it is subsequently inhaled or comes into contact with the recipient's membranes such as open sores, wounds. In fomite transmission, the fomite, an inanimate object or substance capable of carrying infectious organisms, harbors the infections organism on a surface. The second person touches the fomite and subsequently a membranous surface such as the eyes, ear, mouth, or nose, where the contagion enters the system.

The current solutions to contagion spread focus on barriers such as gloves, masks, isolation of the infected individuals, vaccines, and chemical sanitizers or disinfectants. However, those may not be practical as gloves may not be available, not all infected individuals are known, and some people are unable or unwilling to vaccinate or apply sanitizers. For the above reasons, it would be advantageous to have a system and process which minimizes contagion spread via humidification control.

SUMMARY

The present invention is directed to system and process for notification of contagion risk and mitigation of the risk thereof. The system comprises a meteorological history repository having meteorological data and a processor configured with an instruction set. The instruction set includes retrieving meteorological data for a selected region for a selected time window, calculating contagion risk based on the meteorological data and from at least one of a transmission risk or a susceptibility risk, calculating the transmission risk as a function of dew point change and calculating susceptibility risk as a function of relative humidity. The system generates a contagion risk indicator based thereon.

Alternate embodiments of the system mitigate the risk of spread of contagions and comprise a controller having a processor and memory and configured to issue control signals to a humidification unit. The controller is configured to select a lower humidity bound as a function of contagion infectivity and select an upper humidity bound as a function of contagion viability or mold/fungus growth rate. The controller receives humidity data for the sealed area and issues control signals to a humidification unit in response to the received humidity data and according to the selected lower humidity bound and the upper humidity bound.

These and other features, aspects, and advantages of the invention will become better understood with reference to the following description, and accompanying drawings.

BRIEF DESCRIPTION OF THE DRAWINGS

FIG. 1 depicts a block diagram of an embodiment of a system of the current invention;

FIG. 2 depicts an embodiment of the invention as it may exist in operation;

FIG. 3 depicts a representative process according to the current invention;

FIGS. 4*a-b* depict representative output of the embodiment of FIG. 1;

FIG. 5 depicts representative output of the embodiment of FIG. 1;

FIGS. 6*a-c* depict representative output of the embodiment of FIG. 1;

FIG. 7 depicts a block diagram of an embodiment of a system of the current invention;

FIG. 8 depicts a representative process implemented to the embodiment of FIG. 7; and FIGS. 9*a-d* depict relative humidity versus the present of airborne contagions.

DETAILED DESCRIPTION

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

Relative humidity is the ratio of the partial pressure of water vapor in an air-water mixture to the saturated vapor pressure of water at a prescribed temperature. Where "humidity" is used within this specification, it generally refers to relative humidity. The relative humidity of air depends not only on temperature but also on the pressure of the system of interest. However, at or near sea level, pressure variation is minimal and has a negligible impact in relative humidity calculation.

Dew point is the temperature below which the water vapor in air at constant barometric pressure condenses into liquid water at the same rate at which it evaporates. The dew point is associated with relative humidity. A high relative humidity indicates that the dew point is closer to the current air temperature. When the moisture content remains constant and temperature increases, relative humidity decreases.

Current systems and processes for disease transmission are primary retroactive, that is to say that they focus on treatment of the maladie after the spread of a contagion. Attempts at proactive solutions include sanitizers or indicators for specific contagions. The present invention employs a proactive approach to determine a risk of disease transmission. In one aspect, the invention determines a risk of one or more individuals transmitting a contagion. In another aspect, the invention determines a risk of infection of one or more individuals due to susceptibility.

Figure 1:
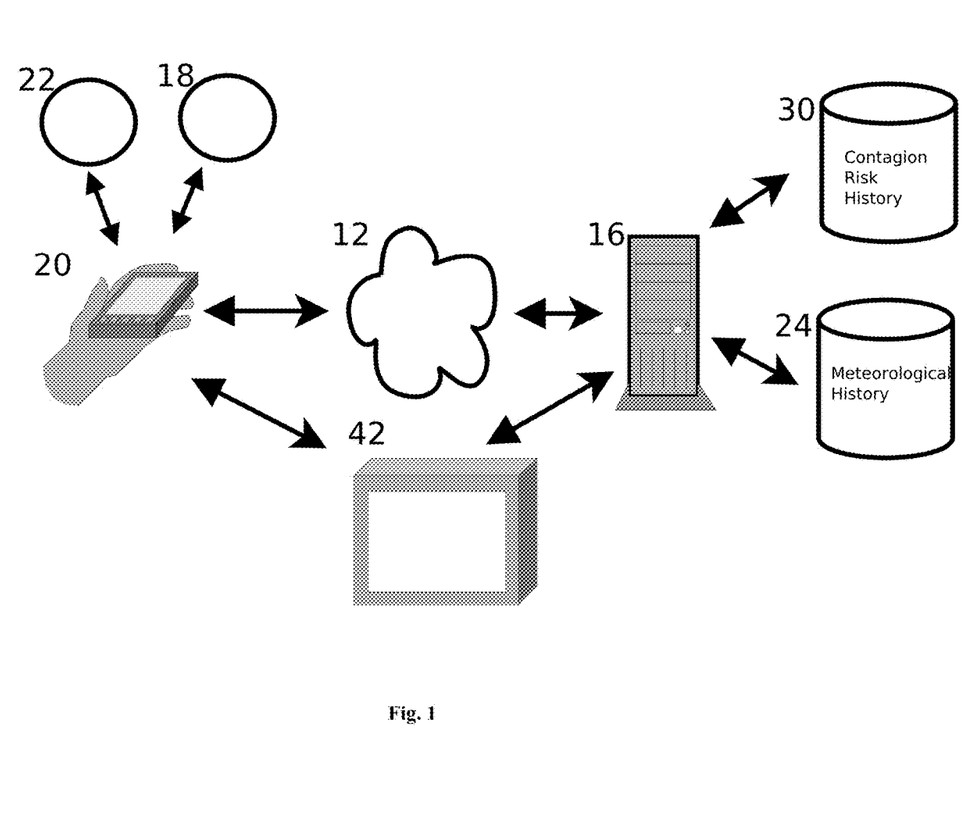
Figure 2:
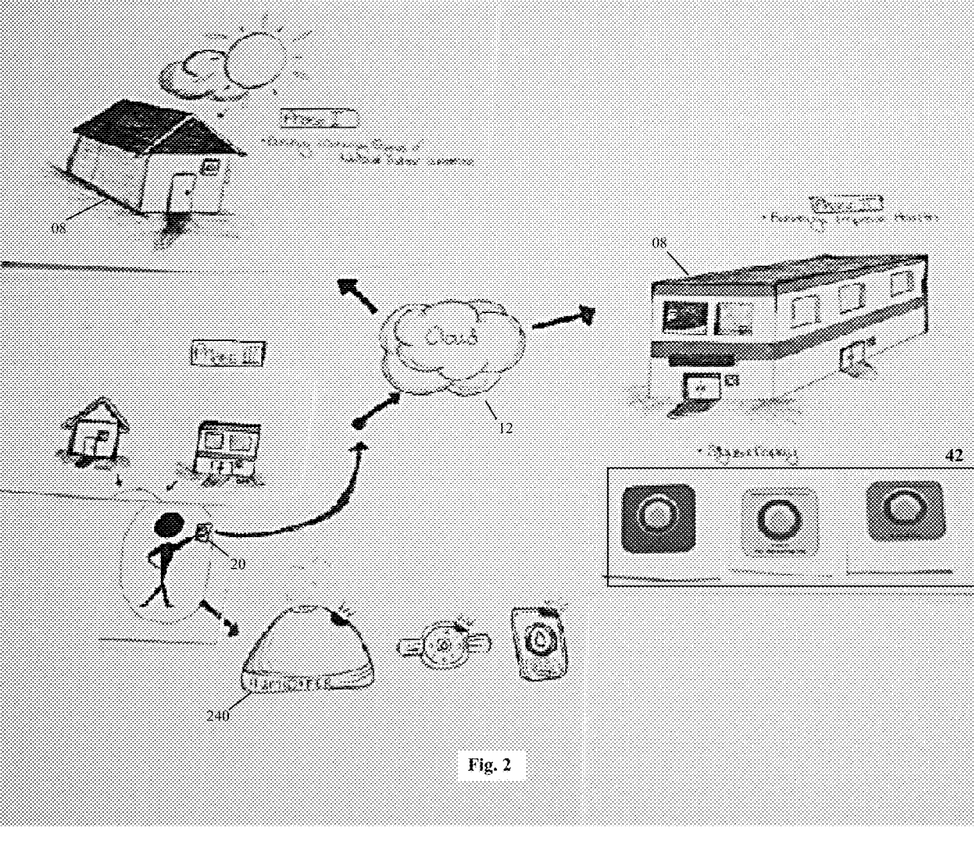

The present invention is directed to systems and processes of calculation and display of risk of disease transmission from meteorological data enabling persons to selectively avoid contact and decrease the chance for infection. FIG. 1 illustrates a block diagram of an embodiment of the system. FIG. 2 illustrates an embodiment of the system of the present invention as it may exist in operation. Depicted are a building 08, a personal computer 20, a network 12, a server 16, a source for meteorological information 08 24, contagion risk storage 30, and a display 42.

The building 08 is a substantially sealed environment, with the common air inflow and outflow sources being a door 04 and ventilation of a heating, ventilation, and air conditioning ("HVAC") system. Representative buildings 08 include hospitals, commercial workplaces, residential settings, or other sealed environments such as an airplane cabin.

The exemplary system 10 includes at least one of a computer 20 or server 16 for communication and storage of the meteorological history 24 and contagion risk 30. A personal computer 20 or server 16, as referred to in this specification generally refers to a system which includes a central processing unit (CPU), memory, an optional screen, a network interface, and input/output (I/O) components connected by way of a data bus. The I/O components may include for example, a mouse, keyboard, buttons, or a touchscreen. The network interface enables data communications over the network 12. A server contains various server software programs and preferably contains application server software such as Microsoft's Internet Information Server. Those skilled in the art will appreciate that server 16 may take a variety of configurations, including personal computers, hand-held devices, multi-processor systems, microprocessor-based electronics, network PCs, minicomputers, mainframe computers, and the like. Additionally, the server 16 may be part of a distributed computer environment where tasks are performed by local and remote processing devices that are linked. Although shown as separate devices, one skilled in the art can understand that the structure of and functionality associated with the aforementioned elements can be optionally partially or completely incorporated within one or the other, such as within one or more processors. The process, or subsets thereof, may exist in a machine-readable medium. The machine-readable medium may include, but is not limited to, floppy diskettes, optical disks, CD-ROMs, and magneto-optical disks, ROMs, RAMs, EPROMs, EEPROMs, magnetic or optical cards, propagation media or other type of media/machine-readable medium suitable for storing electronic instructions. For example, the present invention may be downloaded as a computer program or "app" which may be transferred from a remote computer to a requesting computer by way of data signals embodied in a carrier wave or other propagation medium via a communication link.

The exemplary network 12 includes of a variety of network components and protocols known in the art which enable computers to communicate. The computer network may be a local area network or wide area network such as the internet. The network may include modem lines, high speed dedicated lines, packet switches, telephone lines, etc. The network protocols used may include those known in the art such as UDP, TCP, IP, IPX, or the like. Additional communication protocols may be used to facilitate communication over the computer network, such as the published HTTP protocol used on the world wide web or other application protocols.

Still referring to FIGS. 1 and 2, the system 10 includes historical meteorological data. A key meteorological data element for system processing is the dew point of a selected region. Because dew point, relative humidity, barometric pressure, and temperature are related, the system 10 may receive one or more of those related input data elements. In one configuration, the system retrieves the data elements from a third party sources such as the National Oceanic and Atmospheric Administration, available at http://www.ncdc-.noaa.gov/.

In another configuration, the system 10 is in communication with at least one sensor sensors 18 22 within the selected area, where the effective selected area is a mobile area surrounding a carrier of the sensors 18 22. The exemplary form of this configuration includes a humidity sensor 22. Suitable humidity sensors 22 include capacitive humidity sensors, resistive humidity sensors, thermal conductivity humidity sensors, or other humidity sensors known in the art. The humidity sensor 22 is in communication with the system 10, providing humidity and optional identifier input. The configuration may further incorporate a temperature sensor 18. Suitable temperature sensors 18 include resistance temperature detectors, thermistors, thermocouples, or other temperature sensors known in the art. The temperature sensor 18 is in communication with the system 10, providing local temperature and optional identifier input. In yet another configuration, the system 10 receives data from third party sources and local sensors.

An optional display 42 is in communication with the system 10 in order to display contagion risk output. The display 42 may be integral with the personal computer 20 or server 16 or external.

Figure 3:
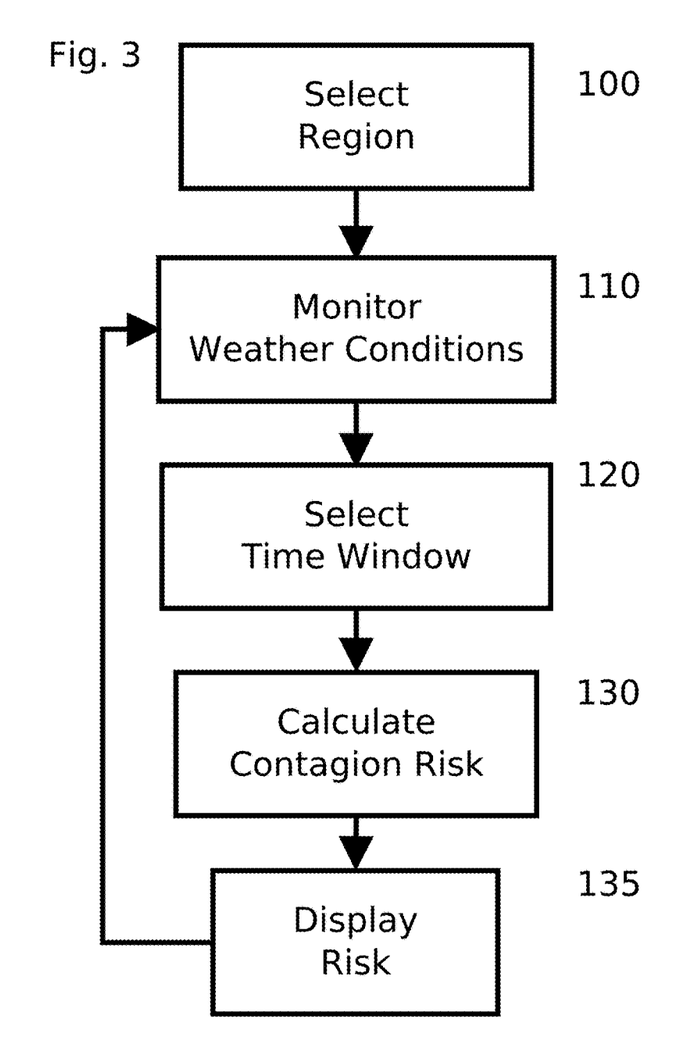

FIG. 3 illustrates a representative process of the current invention. The process includes the steps of selecting a region for determining contagion risk 100. Elements of meteorological data are monitored for the selected region 110. A time window for risk assessment is selected 120. The contagion spread risk is calculated for the selected time window 130. The contagion spread risk is displayed 140. Each of these steps will be considered in more detail below.

At step 100, a region for monitoring contagion risk is selected. The selected region may be a larger area such as a metropolis. An exemplary selected region includes a continuous, generally homogeneous area of generally similar meteorological conditions. The selected region need not be of regular dimensions. In one configuration, the select region is the interior of a building 08. Another representative small region includes an airplane cabin. In another alternate configuration, the selected region is mobile, with the exemplary area being the smaller area proximate an individual.

The meteorological conditions for the selected region are monitored 110. In an exemplary configuration, the dew point is periodically retrieved from a third party source. The system may retrieve readings from one or more samples locations within the selected region. Additionally, system may retrieve relative humidity, temperature, and barometric pressure data from one or more samples within the selected region.

In an alternate embodiment, the meteorological conditions may be retrieved from included sensors 18 22. In one configuration, a humidity sensor 22 is paired and associated with an individual. The humidity sensor 22 may be directly secured to the individual or integrated with a personal computer 20 carried by the individual. Optionally, other sensors such as temperature sensors 18 or barometric sensors may also be paired with the individual.

A time window is selected for calculation of contagion risk 120. The selected time window will be the time period over which the contagion risk is calculated by the system. An exemplary time window can range from about an hour to about a couple of days. A further exemplary can range from several hours to about a day.

The system 10 calculates the contagion risk indicator based on the selected time window 130. The system 10 can calculate contagion risk, primarily employing two approaches. A first contagion risk assessment is susceptibility risk, namely, the risk of an individual becoming infected. A second contagion risk assessment is transmission risk, namely, the risk of an individual spreading a contagion.

The susceptibility risk calculation is based on change in dew point over the selected time window. First, the system 10 calculates the dew point at the beginning of the time window and the end of the time window. In one configuration, the current and future projected dew point temperatures are directly retrieved from third party sources. In another configuration, the relative humidity may be retrieved from a third party source. In yet another configuration, the humidity is retrieved from the humidity sensor 22 and converted to relative humidity. In yet another configuration, the system 10 receive at least one of relative humidity and temperature. The system 10 employ conversions known in the art to convert the input to dew point. One such well-known approximation for solving for unknown relative humidity, temperature, or dew point is the Magnus formula:

It is within the spirit of this invention to employ modifications to the above formula, such as the Arden Buck equation, or other alternate formulae. It is also within this spirit of this invention to assume or certain variables in calculation for efficiency or $$\gamma(T, RH) = \ln\left(\frac{RH}{100}\exp\left(\frac{bT}{c+T}\right)\right) = \ln\left(\frac{RH}{100}\right) + \frac{bT}{c+T};$$

$$T_{dp} = \frac{c\gamma(T, RH)}{b - \gamma(T, RH)};$$

availability. For example, the system may assume a constant pressure within a range of about 1000 feet from sea level for the subject area of interest. For example, it may assume outdoor relative humidity substantially equals indoor relative humidity (or a negligible difference) under normal HVAC operation. For example, it may assume outdoor dew point temperature substantially equals indoor dew point temperature (or a negligible difference) under normal heating, ventilation, and air conditioning (HVAC) operation.

After any necessary conversions to dew point temperature, the difference between the dew point temperatures is calculated with the exemplary output units being degrees or degree per day or other selected time interval.

Figure 4A:
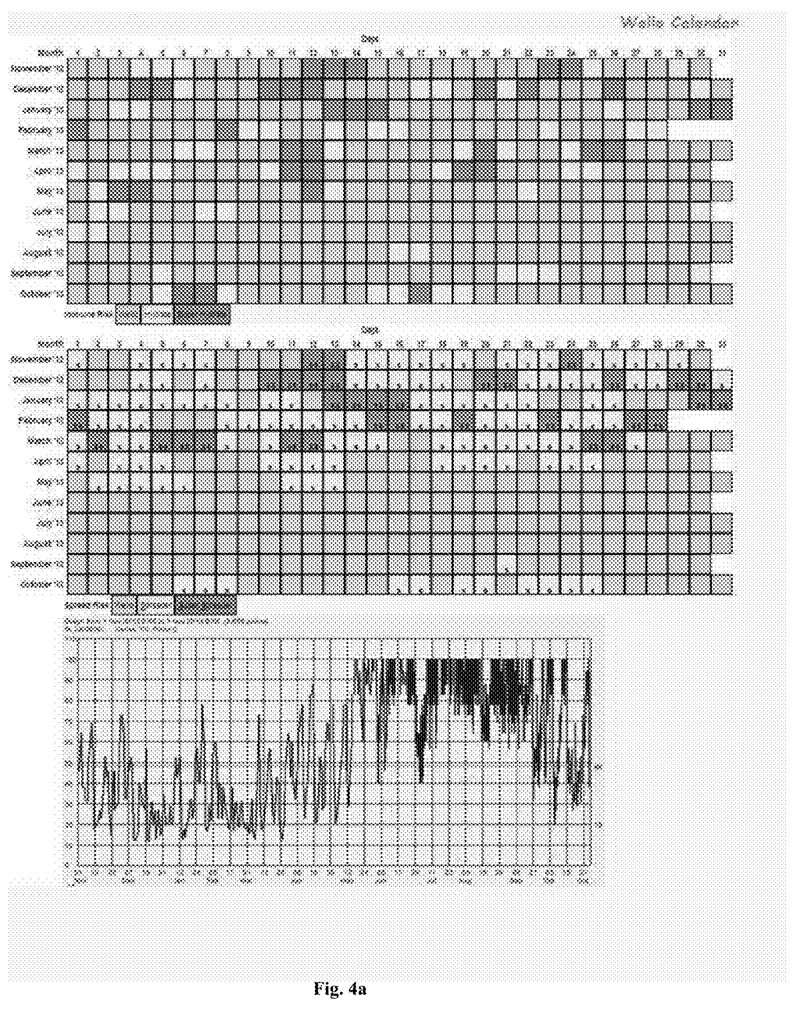
Figure 4B:
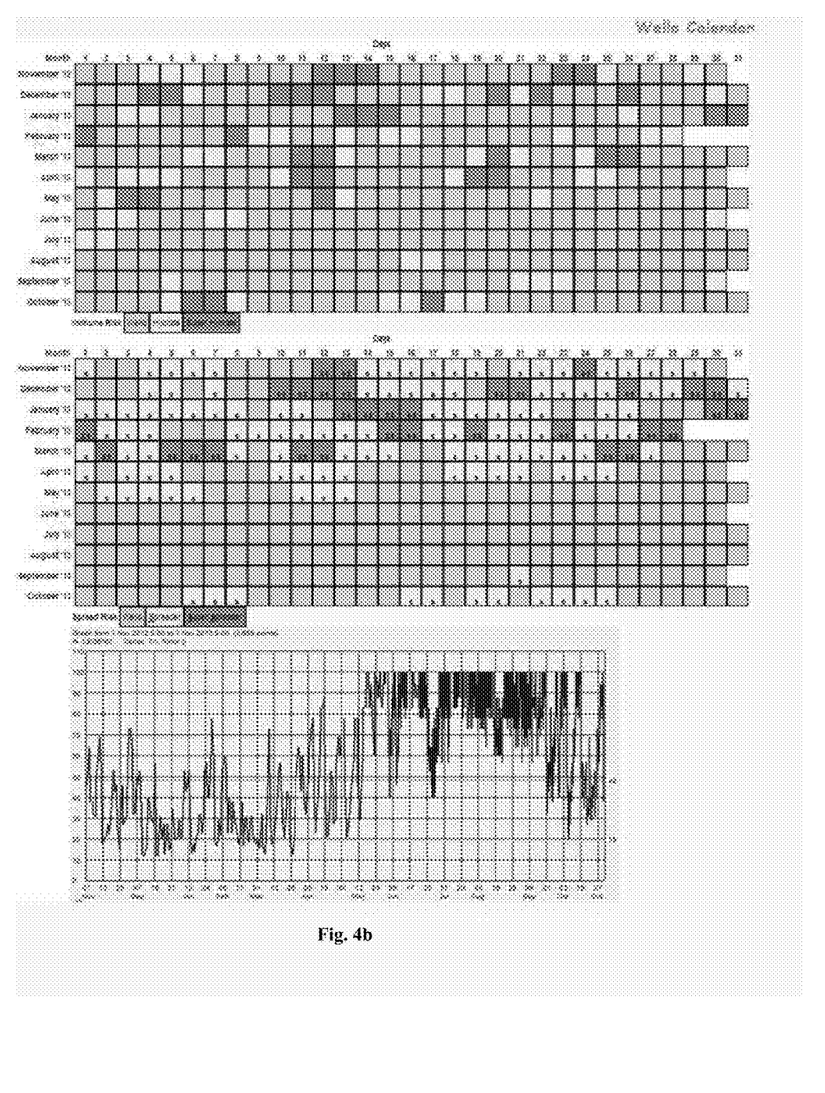

FIGS. 4a and 4b show a representative changes in dew point for given time windows. The transmission or "spread" risk is calculated based on a modified relative humidity value within the selected time window. First, the system 10 receives or calculates a dew point temperature within the time window. The dew point temperature is converted to a relative humidity value as known in the art and previously disclosed. In an exemplary configuration, the input dew point temperature is converted to relative humidity with the system assuming a temperature of 70° F.

The risk assessment output is stored in the contagion risk history 30 database.

After calculation of the contagion risk assessments, those risk assessments (susceptibility risk and transmission risk) are transmitted for display or displayed 140. Each of the contagion risk assessments is displayed separately and optionally in different styles. Further, the risk assessments display 42 may be triggered upon preset conditions, continuously displayed, or displayed on demand. In one configuration, each of the reports is sent to the display 42 as a tabulated list of numbers. In another configuration, the raw numeric output is scaled prior to display. In yet another configuration, the numbers are grouped into preset ranges of risk level and assigned corresponding indicia. It should be appreciated that the formats can be combined or other approaches known in the art can be employed.

In FIGS. 4a and 4b, exemplary output is shown, with the uppermost charts illustrate susceptibility risk ("immune risk"). The reports include meteorological data from a third party source and the representative selected time window is one day. The dew point temperature changes over the selected single day time window are grouped into preset risk ranges. The lowest risk range includes dew point temperature changes that are positive or less than five degree decrease. The mid-risk range includes dew point temperature changes that are between a five degree decrease and a sixteen degree decrease. The highest risk group includes dew point temperature decreases that are greater than sixteen degrees. The lower risk range is assigned a green color, the mid-risk range is assigned a yellow color, and the highest risk range is assigned a red color. The colors are overlaid on a calendar style view.

In FIGS. 4a and 4b, the middle charts illustrate transmission risk. The reports include meteorological data from a third party source and the modified relative humidity is selected within the day. The modified relative humidity values are grouped into preset risk ranges. The lowest risk range includes modified relative humidity values that are greater than 48. The mid-risk range includes modified relative humidity values that are between twenty and forty-eight. The highest risk group includes modified relative humidity values that are less than twenty. The lower risk range is assigned a green color, the mid-risk range is assigned a yellow color, and the highest risk range is assigned a red color. The color are overlaid on a calendar style view.

Figure 5:
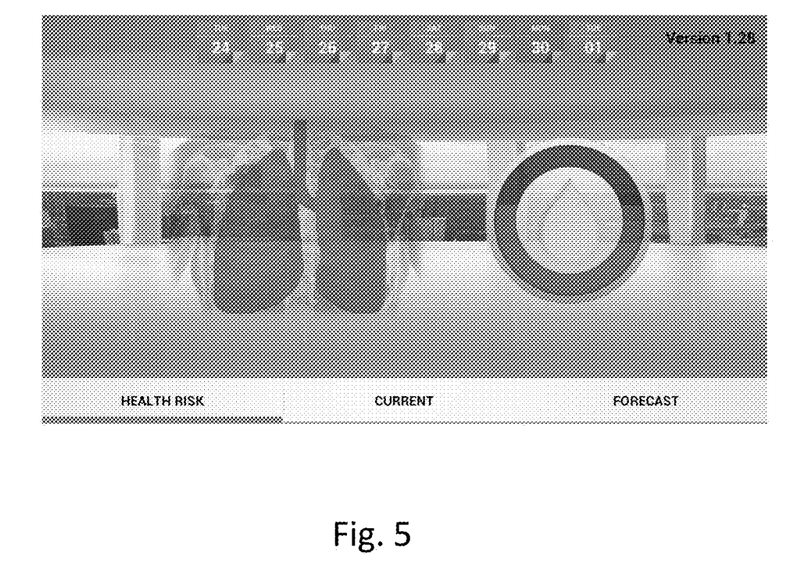
Figure 6A:
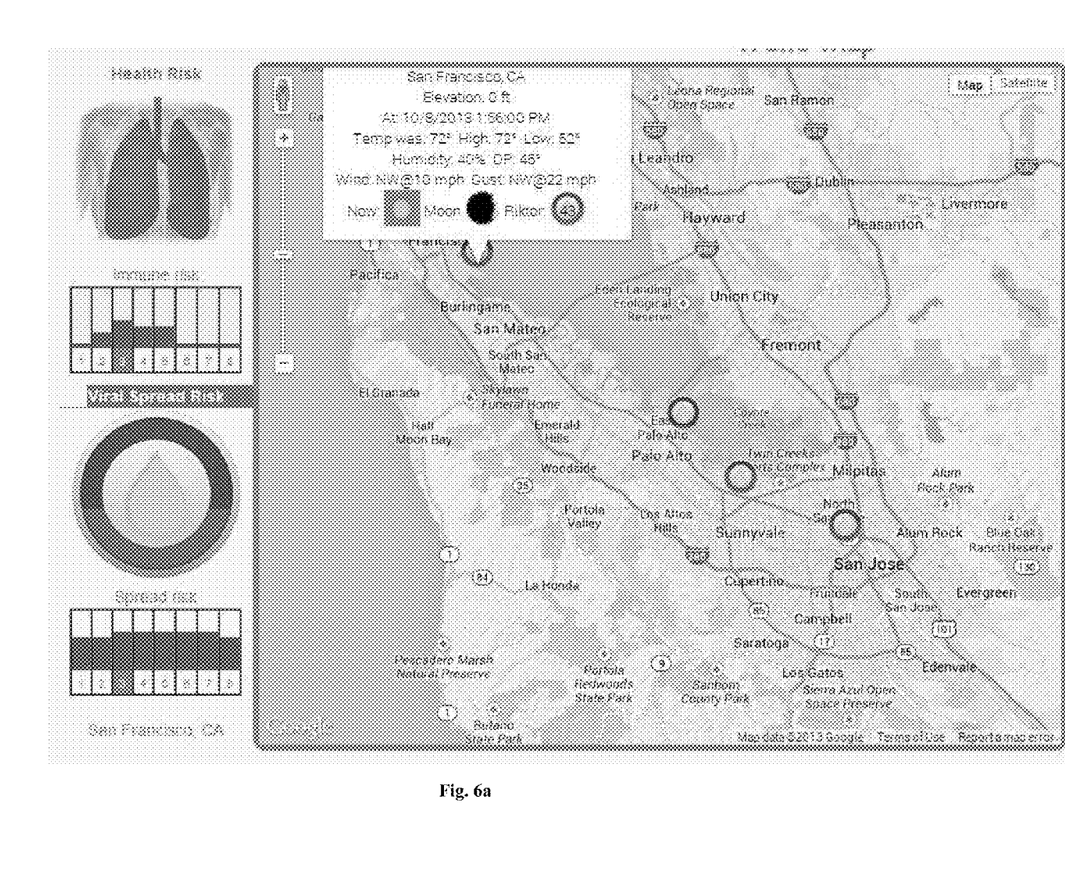
Figure 6B:
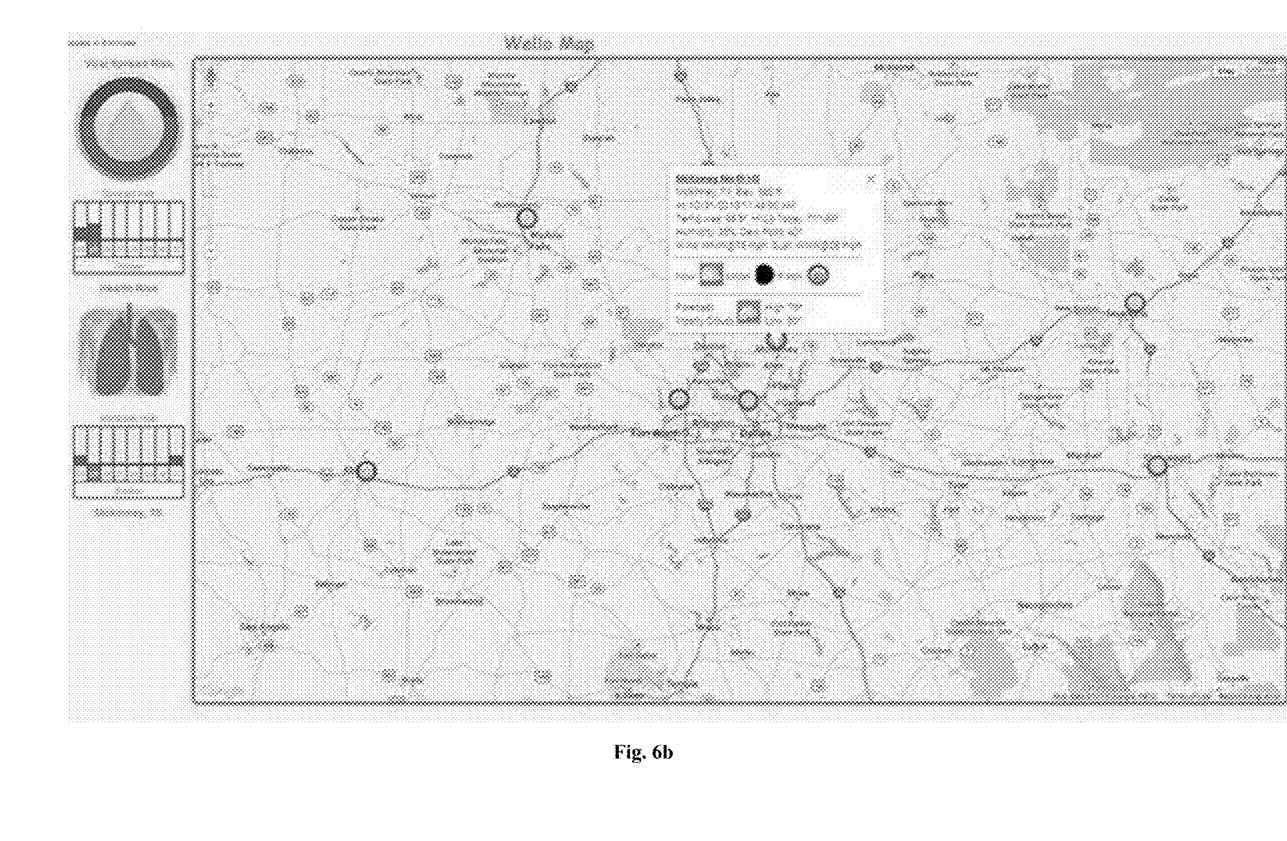
Figure 6C:
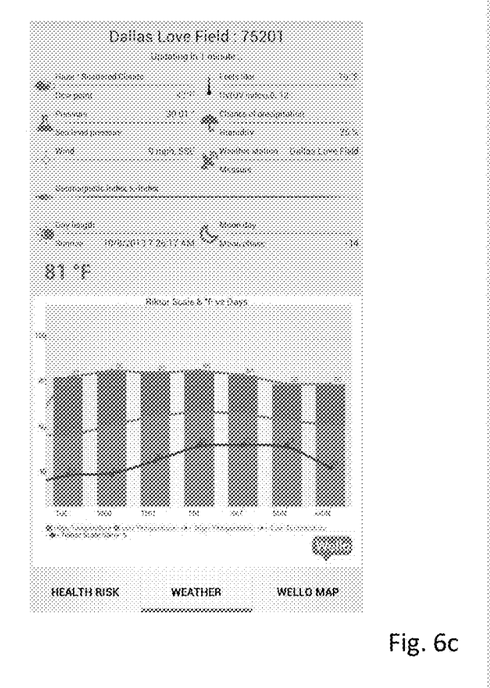

FIG. 5 illustrates the two risk assessments where the risk ranges of each are assigned a specific icon. FIGS. 6a-6c illustrate the two risks assessments with a raw number, an icon, a scaled color range, and the associated selected region.

It is also within the spirit of this invention to alter the humidity in order to control an HVAC system in response to contagion spread conditions. For example, the system may alter the humidity, and in turn the related conditions, of the enclosed environment in order to minimize spread conditions. For example, where the selected region is an airplane cabin for a long flight, the system may alter the interior humidity to minimize, for example, dew point change for a time window. It may supplement the conditions of the airplane cabin with meteorological conditions of the airport of departure or arrival. As another example, where the selected region is the ambient environment of a user, the system may use the historical conditions for that person as input and control the HVAC of that persons home in order to minimize, for example, dew point change. Further disclosure of HVAC control is included in an appendix.

Alternate embodiments of this invention disclose mitigation of the risk of contagion spread. Relative humidity is the ratio of the partial pressure of water vapor in an air-water mixture to the saturated vapor pressure of water at a prescribed temperature. Where "humidity" is used within this specification, it generally refers to relative humidity. The relative humidity of air depends not only on temperature but also on the pressure of the system of interest. Modeling indicates that humidity presents containment for airborne viruses. Accordingly, viruses remain airborne longer and with more viability in lower relative humidity.

As previously disclosed, the dew point is the temperature below which the water vapor in a volume of humid air at a given constant barometric pressure will condense into liquid water at the same rate at which it evaporates. The dew point is a water-to-air saturation temperature. The dew point is associated with relative humidity. A high relative humidity indicates that the dew point is closer to the current air temperature. Relative humidity of 100% indicates the dew point is equal to the current temperature and that the air is maximally saturated with water.

Temperature, dew, point, and relative humidity are interrelated. If two of the variables are known, the other can be solved. It should be appreciated that even where one variable is known, the other may be approximated, in turn leading to solving for the third variable. For example, air inside the subject environment and adjacent air outside but adjacent can be assumed to have similar dewpoints, where the indoor air is slightly lower (drier) by virtue of indoor heating or cooling. From assumptions such as these, the system may make calculations for indoor air based on data, adjusted or otherwise, from outdoor air conditions from current meteorological conditions. The system may do so for dewpoint or other data points.

Well-known approximations for solving for unknown relative humidity, temperature, or dew point is the Magnus formula. It is within the spirit of this invention to employ modifications to the above formula, such as the Arden Buck equation, or alternate formulae.

In lower humidity, contagions have a higher survivability rate when expelled from the body in saline mucous droplets from exhaling, coughing, or sneezing. It is believed that in lower humidity the expelled saline mucous dries rapidly while still airborne. In such dry air rapid evaporation occurs crystallizing the salt separating the contagion where the contagion is more easily spread and a larger population is viable for infection. In higher humidity, the contagions remains in solution with the salt water for longer periods, in increasingly saltier brine thusly killing a higher percentage of them.

However, too high a relative humidity promotes the growth of fungus, mold and permits contagion in saline solution to now be viable since evaporation no longer occurs. This invention maintains an environment within a configured safe range bounded by an upper and lower limit Maintaining an environment within this desired humidity range can be a preventative measure against contagion spread or through moisturizing the membranes of the people working or visiting the building, less likely to take hold. Then other factors such as energy consumption, water consumption, may be considered in maintaining the environment within that configured range of humidity.

Figure 7:
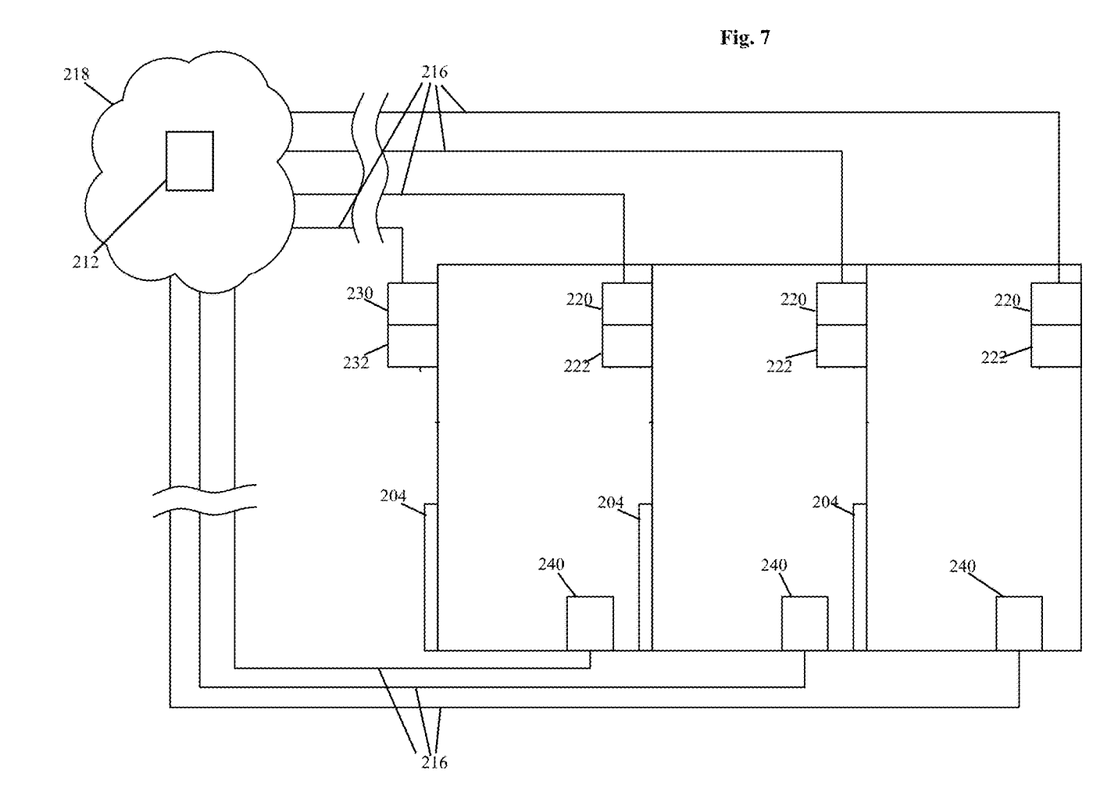

The present embodiments are directed to a system and process of control of humidity in an environment in order to minimize contagion spread. FIG. 7 illustrates an embodiment of the system of the present invention. Depicted are a building 208, an outdoor humidity sensor 230, an outdoor temperature sensor 232, a plurality of indoor humidity sensors 220, a plurality of indoor temperature sensors 222, a humidifier 240, and a controller 212.

The building 208 is a substantially sealed environment, with the relevant air inflow and outflow sources being a door 204 and ventilation of an HVAC system. Suitable buildings 208 include hospitals, commercial workplaces, residential settings, or other sealed environments such as an airplane cabin. The building 208 may be further subdivided into rooms 206, to which individual humidity control can be applied. The system further includes at least one indoor humidity sensor 220 operable to measuring the moisture content in the air inside the subject environment 206. Suitable indoor humidity sensors 220 include capacitive humidity sensors, resistive humidity sensors, thermal conductivity humidity sensors, or other humidity sensors known in the art. In exemplary use, an indoor humidity sensor 220 is deployed to each room 206. The indoor humidity sensor 220 is in communication with a controller 212 via a communication line 216, providing humidity and identifier input to the controller 212.

Proximate the indoor humidity sensor 220 is at least one indoor temperature sensor 222 operable to measure the temperature. Suitable indoor temperature sensors include resistance temperature detectors, thermistors, thermocouples, or other temperature sensors known in the art. The indoor temperature sensor 222 is in communication with a controller 212 via a communication line 216, providing temperature and identifier input to the controller 212.

The system further optionally includes at least one outdoor humidity sensor 230, operable to measuring the moisture content of the air outside the building 208. Suitable outdoor humidity sensors 230 include capacitive humidity sensors, resistive humidity sensors, thermal conductivity humidity sensors, or other humidity sensors known in the art. In exemplary use, an outdoor humidity sensor 230 is secured proximate the possible air inflow into the building 208, namely the door 204 and/or ventilation. The outdoor humidity sensor 230 is in communication with a controller 212 via a communication line 216, providing humidity and identifier input to the controller 212.

Proximate the outdoor humidity sensor 230 is an outdoor temperature sensor 232 operable to measure the temperature outside the building 208. Suitable outdoor temperature sensors include resistance temperature detectors, thermistors, thermocouples, or other temperature sensors known in the art. The outdoor temperature sensor 232 is in communication with a controller 212 via a communication line 216, providing temperature and identifier input to the controller 212.

In exemplary operation, a humidification unit 240 is deployed within each room 206 of building 208. As used within this specification, the humidification unit 240 acts as both a humidifier and a dehumidifier. Although the humidification unit 240 is depicted as a discrete unit, it should be understood that it may be integrated with the building's 208 heating, ventilation, and air conditioning (HVAC) system. The humidification unit 240 is in communication with a controller 212 via a communication line 216, receiving control signals from the controller 212.

The controller 212 includes a processor and memory to process and store environmental information. The exemplary processor includes an instruction set to at least receive sensor 220 222 230 232 input, receive third-party meteorological input, store and retrieve sensor 220 222 230 232 input, store and retrieve third-party meteorological input, process sensor 220 222 230 232 input, process third-party meteorological input, and issue control signals to the humidification unit 240.

The communication line 216 is a communication link between devices. As shown, it includes a conductive cable between devices. It should be appreciated that the link can also be wireless. In exemplary operation, the devices 212 220 222 230 232 240 are linked over a network 218. The network 218 includes of a variety of network components and protocols known in the art which enable devices 220 222 230 232 240 and controller 212 to communicate. The network 218 may be a local area network or wide area network such as the internet.

Figure 8:
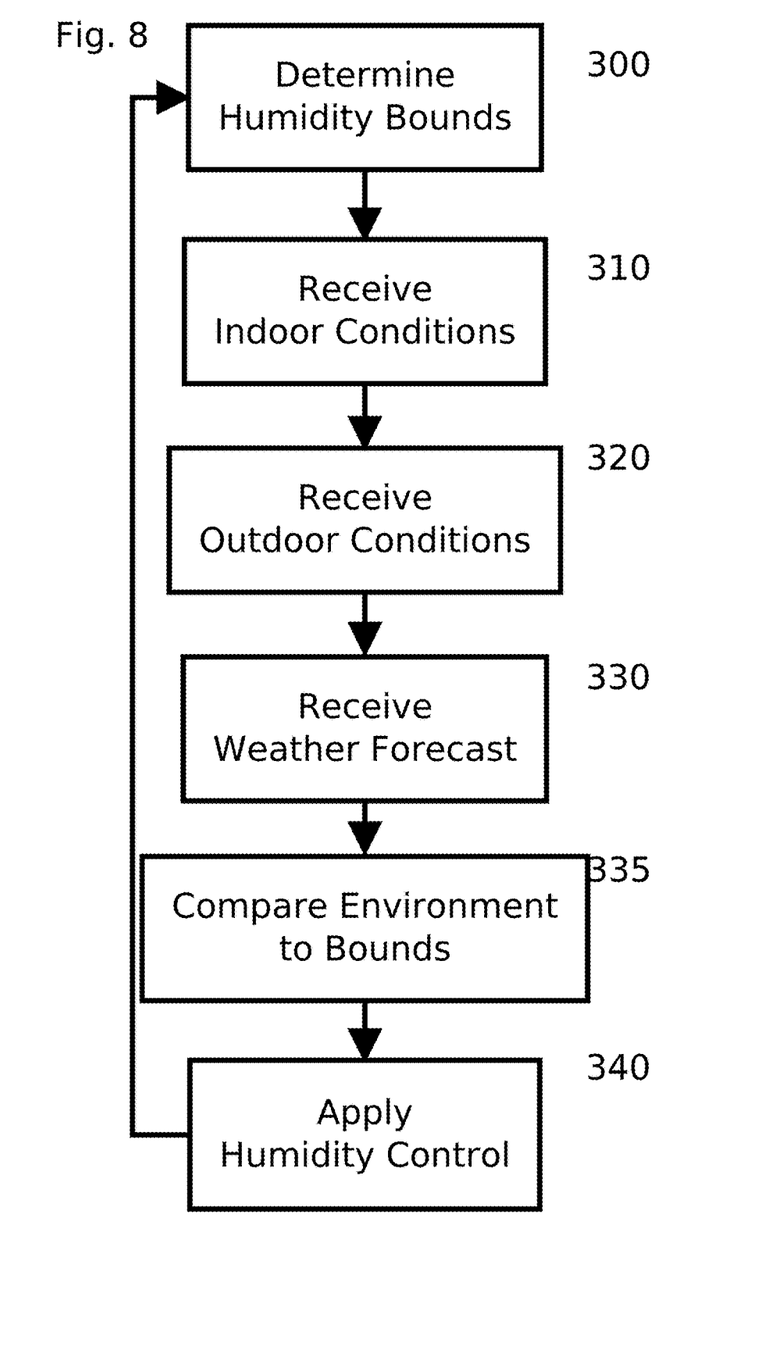

A process of humidification control is implemented to a humidification monitoring and control system in order to minimize the spread of contagions. FIG. 8 illustrates a representative control process. The process determines acceptable lower and upper bounds of humidity for the environment 300. The current humidity conditions of the environment are received 310. The outdoor conditions adjacent to the environment are received 320. The weather forecast for the region is received 330. The controller 212 compares the environmental humidity to the determined bounds 335. The humidification system is controlled accordingly 340. Each of these steps will be considered in more detail below.

The controller 212 determines suitable lower and upper humidity bounds for the environment 300. In determining the lower humidity bound, two key factors are used in this stage of the process. The first factor focuses on reducing airborne contagion spread by containing mucous expelled by actions such as person's exhalation. A second factor focuses on fomite transmission and is considered by the process by optimally selecting a humidity to exploit the toxicity of the salt in the mucous to the contagion, as previously disclosed. For this factor, the exemplary are higher and trend towards much higher thresholds upwards of about 85%.

The second factor exploits contagion to humidity contact such that the humidity binds the contagion, whereby the possibly of airborne transmission is limited. Research was carried out to determine effective minimum humidity. Airborne contagion transmission was simulated with particles of varying sizes at various humidity and the percentage infectivity measured. FIG. 9d shows contagions of <1 µm. FIG. 9c shows contagions of 1-4 µm. FIG. 9b shows contagions of >4 µm. FIG. 9a shows aggregate data FIGS. 9b-9d. The exemplary minimum humidity for this factor of the process for aggregate contagions is about >=42%. It should be appreciated that the effective minimum can be varied based on the size of a particular contagion of concern. A humidity of 42% is able to reduce the spread of contagion by 90% or more over humidity of 32%.

In exemplary configuration, the greater of the two minimum humidity numbers from the initial two factors is selected as the base minimum humidity. While the exemplary minimum humidity is about 42% increases in viral kill (loss of viral infectious viability) increases further with humidity up to about 85%.

The controller 212 determines a suitable upper bound for humidity for the environment 206. In determining the upper bound, two key factors are used in the process. The first factor focuses on reducing contagion spread by the contagion containing mucous expelled by a person's sneeze, cough, or exhalation. The process optimally selects a maximum humidity to exploit the toxicity of the salt in the mucous to the contagion, as previously disclosed. For this factor, the exemplary configuration applies a maximum of about a 85% upper humidity bound threshold.

The second factor seeks to minimize mold and fungus growth. For this factor, the exemplary process applies a maximum of about a 70% upper humidity bound threshold.

In exemplary configuration, the lower of the two maximum humidity numbers from the initial two factors is selected as the maximum humidity. The exemplary maximum humidity is about 70%.

The controller 212 queries the indoor humidity and temperature sensors 220 222 and receives current temperature and humidity data for the room 206 310. The controller 212 queries the outdoor humidity and temperature sensors 230 232 and receives current temperature and humidity data for the outdoor environment adjacent to the subject environment 320. Optionally, the controller 212 receives near term weather forecast information, including temperature, humidity, dew point, and pressure data. The indoor conditions, outdoor conditions, and weather forecast data are stored for later processing and reporting. In an alternate configuration, the controller 212 queries current meteorological data proximate the subject environment for outdoor conditions. This query may be address, weather station, zip code, or other keys. In the alternate configuration, indoor conditions might be received from alternate inputs, such as a thermostat. The controller 212 may adjust or derive conditions based on correlations between indoor and outdoor conditions or similar approaches.

As people use to enter and exit via the door 204, people exhale, and people perspire, the humidity of the environment changes. The controller 212 receives sensor 220 222 input to continually monitor and detect the changed humidity of the environment 206. The controller 212 compares the indoor humidity to the determined bounds 335. As disclosed above, system optionally also receives near term weather forecast information. The controller 212 monitors whether the environment is within the proscribed range or whether potential environment changes can bring the environment out of range and can signal a current out of range condition or future out of range condition.

In one configuration, the controller 212 prepares information for display as a notice or warning based on the environment and likelihood of contagion spread. The exemplary information for display includes a risk of spread indicator, viability indicator, and a risk of epidemic indicator. The risk of spread indicator and viability indicator are based upon two primary factors, namely the relative humidity and percentage infectivity. Representative information for which the primary two factors is shown in FIGS. 9a-d.

The risk indicator may be numerical, such as percent infectivity or a scale. It might also be grouped in a manner such as low, medium, or high. It can be represented as a color.

In another configured response to an out of range state or future out of range condition, the controller 212 issues controls signals to the humidification unit 240 to keep the system within the upper and lower bounds and towards a resting humidity. The controller 212 sends control signals to the humidification unit 240 to control the humidity in the environment and keep it within the determined bounds 340. The controller 212 sends control signals to keep the humidity within the upper and lower bounds. The controller 212 may seek to keep the environment at a configured resting humidity, that is a specific humidity or more narrow range than the upper and lower bound. The exemplary resting humidity is about 50%, however the system may deviate from the exemplary resting humidity based on the following nonexclusive factors: cost and availability of water, cost and availability of power, instantaneous and near term power demand, expected door 204 usage, expected dry or humid weather conditions, rate of humidification or dehumidification of the humidification unit 240, the current humidity's proximity to the upper or lower bound.

For example, the weather forecast may show a coming rapid change in weather. A rapid increase in humidity could overburden the humidification unit 240 leading to indoor humidity greater than the selected upper bound. Likewise, a rapid decrease in humidity could also overburden the humidification unit 240 leading to indoor humidity lower than the selected lower bound. In such a circumstance, the system may send control signals for dehumidification to the lower bound in order to compensate for the anticipated additional humidity from the forecast, receiving interior room 206 or building 208 volume, air inflow or outflow rates, and/or humidification/dehumidification rates. Thus when the anticipated additional outdoor humidity arrives and mixes with the indoor air, the humidity of the indoor system is still within the determined bounds.

The system then reiterates through the steps of receiving current humidity conditions of the environment 310, receiving outdoor conditions adjacent to the environment 320, receiving the weather forecast for the region 330, and controlling the humidification system 340.

Insofar as the description above and the accompanying drawing disclose any additional subject matter that is not within the scope of the single claim below, the inventions are not dedicated to the public and the right to file one or more applications to claim such additional inventions is reserved.

What is claimed is:

1. A system for notification of contagion spread risk, the system comprising:
    a meteorological history repository having meteorological data;
    a processor configured with an instruction set of:
    retrieving meteorological data for a selected region for a selected time window;
    calculating said contagion spread risk based on said meteorological data from a transmission risk;
    calculating said transmission risk as a function of dew point change; and
    generating a contagion risk indicator for said selected region for said selected time window; and further providing a temperature sensor or humidity sensor associated with a person and in communication with said processor, wherein said meteorological history comprises said temperature sensor or said humidity sensor data.

2. A system for mitigating the spread of contagions in a sealed area, the system comprising:

a controller having a processor and memory and configured to issue control signals to a humidification unit;

said controller configured to select a lower humidity bound as a function of contagion infectivity;

said controller configured to select an upper humidity bound as a function of contagion viability or mold/fungus growth rate;

said controller receiving humidity data for said sealed area; and said controller issuing control signals to a humidification unit in response to said received humidity data according to said selected lower humidity bound and said upper humidity bound, wherein said lower bound is about 40% and said upper bound is about 70%.

3. A method for mitigating the spread of contagions in a sealed area, the method comprising:

providing a controller having a processor and memory and configured to issue control signals to a humidification unit;

said controller selecting a lower humidity bound as a function of contagion infectivity;

said controller selecting an upper humidity bound as a function of contagion viability or mold/fungus growth rate;

said controller receiving humidity data for said sealed area; and said controller issuing control signals to a humidification unit in response to said received humidity data according to said selected lower humidity bound and said upper humidity bound, wherein said lower bound is about 40% and said upper bound is about 70%.

4. A system for notification of contagion risk, the system comprising:

a meteorological history repository having meteorological data;

a processor configured with an instruction set of:

retrieving meteorological data for a selected region for a selected time window;

calculating contagion risk based on said meteorological data from susceptibility risk;

calculating said susceptibility risk as a function of relative humidity; and generating a contagion risk indicator for said selected region for said selected time window; and further providing a temperature sensor or humidity sensor associated with a person and in communication with said processor, wherein said meteorological history comprises said temperature sensor or said humidity sensor data.

* * * * *